(12) United States Patent
Sun et al.

(10) Patent No.: US 11,516,976 B2
(45) Date of Patent: Dec. 6, 2022

(54) IRRIGATION SYSTEM CONTROL WITH PREDICTIVE WATER BALANCE CAPABILITIES

(71) Applicant: THE TEXAS A&M UNIVERSITY SYSTEM, College Station, TX (US)

(72) Inventors: Lijia Sun, College Station, TX (US);
Jiang Hu, College Station, TX (US);
Dana O. Porter, Wolfforth, TX (US);
Thomas H. Marek, Amarillo, TX (US);
Charles C. Hillyer, Amarillo, TX (US);
Yanxiang Yang, College Station, TX (US)

(73) Assignee: The Texas A&M University System, College Station, TX (US)

( * ) Notice: Subject to any disclaimer, the term of this patent is extended or adjusted under 35 U.S.C. 154(b) by 276 days.

(21) Appl. No.: 16/771,321

(22) PCT Filed: Dec. 11, 2018

(86) PCT No.: PCT/US2018/064949
§ 371 (c)(1),
(2) Date: Jun. 10, 2020

(87) PCT Pub. No.: WO2019/118460
PCT Pub. Date: Jun. 20, 2019

(65) Prior Publication Data
US 2020/0296906 A1 Sep. 24, 2020

Related U.S. Application Data

(60) Provisional application No. 62/597,048, filed on Dec. 11, 2017.

(51) Int. Cl.
*A01G 25/16* (2006.01)
*G06N 20/00* (2019.01)
(Continued)

(52) U.S. Cl.
CPC ......... *A01G 25/165* (2013.01); *A01G 25/167* (2013.01); *G01N 33/246* (2013.01); *G06N 20/00* (2019.01); *G01N 2033/245* (2013.01)

(58) Field of Classification Search
CPC .. A01G 25/165; A01G 25/167; G01N 33/246; G01N 2033/245; G06N 20/00;
(Continued)

(56) References Cited

U.S. PATENT DOCUMENTS

2018/0211156 A1* 7/2018 Guan .................. G06N 3/0445

OTHER PUBLICATIONS

Shivaram Irukula, "Reinforced Learning Based on Controller for Precision Irrigation," A Dissertation Submitted to the Office of Graduate and Professional Studies of Texas A&M University, Dec. 2015. (Year: 2015).*

* cited by examiner

*Primary Examiner* — Chad G Erdman
(74) *Attorney, Agent, or Firm* — Thomas | Horstemeyer, LLP

(57) ABSTRACT

Disclosed are various embodiments for reinforcement learning-based irrigation control to maintain or increase a crop yield or reduce water use. A computing device may be configured to determine an optimal irrigation schedule for a crop planted in a field by applying reinforcement learning (RL), where, for a given state of a total soil moisture, the computing device performs an action, the action comprising waiting or irrigating crop. An immediate reward may be assigned to a state-action pair, the state-action pair comprising the given state of the total soil moisture and the action performed. The computing device may instruct an irrigation system to apply irrigation to at least one crop in accordance with the optimal irrigation schedule determined, where the optimal irrigation schedule includes an amount of water to be applied at a predetermined time.

20 Claims, 11 Drawing Sheets

(51) Int. Cl.
*G01N 33/24* (2006.01)
*G06N 3/04* (2006.01)

(58) Field of Classification Search
CPC ........ G06N 3/08; G06N 7/005; G06N 3/0454; G06Q 50/02
See application file for complete search history.

```
1: function SIMUTSW(i, a) // i is time step, a ∈ A
2:     j = (i − 1) * 3 + 1 // j is index of days
3:     I_j ← IrrigationAmount(TSW_j, TFP_a, Weather)
4:     if I_j < 20 then
5:         I_j ← 0
6:     end if
7:     for k = j + 1, k++, while k < j + 4 do
8:         TSW_k ← PredTSW(TSW_{k−1}, I_{k−1}, ET_{k−1}, R_{k−1})
9:     end for
10:    return TSW_{j+3} and I_j
11: end function
```

```
   Initialize Q(s,a) arbitrarily
2: repeat
      for all e(s,a) do
4:        e(s,a) ← 0 //Initialize eligibility trace
      end for
6:    for i = 1, i++, while i < n + 1 do
         s ← State(i, TSW_i);
8:       Take action a
         [TSW_i + 1, I_i] ← SimuTSW(i, a)
10:      s' ← State(i, TSW_i);
         a' ← greedy(ε, Q, S_{i+1})
12:      if i < n then
            r ← 0
14:      else
            W ← Sum(I) * WaterPrice
16:         Y ← PredYield(TSW) * ProductPrice
            NetReturn ← Y - W
18:         if NetReturn < threshold then
               r ← -50
20:         else
               r ← NetReturn
22:         end if
         end if
24:      δ ← r + γQ(s',a') - Q(s,a)
         e(s,a) ← e(s,a) + 1
26:      for all s and a do
            Q(s,a) ← Q(s,a) + αδe(s,a)
28:         e(s,a) ← γλe(s,a)
         end for
30:      a ← a'
      end for
32: until Q(s,a) converges or policy sufficiently stabilized
```

*FIG. 7*

IRRIGATION SYSTEM CONTROL WITH PREDICTIVE WATER BALANCE CAPABILITIES

CROSS-REFERENCE TO RELATED APPLICATIONS

This application is the § 371 national phase application of PCT/US2018/064949, filed Dec. 11, 2018, which claims the benefit of and priority to U.S. Provisional Patent Application No. 62/597,048 entitled "IRRIGATION SYSTEM CONTROL WITH PREDICTIVE WATER BALANCE CAPABILITIES," filed on Dec. 11, 2017, the contents of which being incorporated by reference in their entirety herein.

BACKGROUND

Irrigation management plays a critical role in determining crop yield. Crop yield largely depends on a sufficient water supply. Yet, fresh water resources are limited. Ideally, farmers irrigate an exact amount of water that is needed by crop, no more and no less. Historically, such precise irrigation control is complex and difficult, if not impossible. However, currently, wireless sensors, computer networking, and advanced irrigation machines enable site-specific variable rate irrigation (SSVRI), making precise irrigation control realistic.

In artificial intelligence and machine learning applications, reinforcement learning (RL) relates to an area of computer engineering and science concerned with how an artificial intelligence application should take actions in an environment so as to maximize a reward. Like a human, an artificial intelligence routine may apply reinforcement learning to achieve successful strategies that lead to long-term rewards based on trial-and-error. For instance, a decision made by the artificial intelligence application may cause the application to receive either a reward or a punishment.

BRIEF SUMMARY OF INVENTION

According to a first embodiment, a system for reinforcement learning-based irrigation control is described to maintain or increase a crop yield or reduce water use. The system includes at least one computing device and program instructions stored in memory and executable by the at least one computing device that, when executed, direct the at least one computing device to: determine an optimal irrigation schedule for at least one crop in at least one region of a field by executing a reinforcement learning (RL) routine, where, for a given state of a total soil moisture, the reinforcement learning (RL) routine is configured to: perform an action, the action comprising waiting or irrigating the at least one crop; and assign a reward (e.g., an immediate reward or a delayed reward) to a state-action pair, the state-action pair comprising the given state of the total soil moisture and the action performed; and instruct an irrigation system to apply irrigation to at least one crop in accordance with the optimal irrigation schedule determined, wherein the optimal irrigation schedule comprises an amount of water and a determined time at which the amount of water should be applied.

The optimal irrigation schedule may be determined using at least one of: a real-time soil moisture value, a near real-time soil moisture value, a predictive evapotranspiration (ET) metric, or a weather forecast metric. The system may further include a cascading neural network configured to generate a crop yield. The cascading neural network configured to generate the crop yield may include: a first neural network configured to receive, as an input, at least one of irrigation data and weather data, wherein the first neural network is configured to provide a total soil water (TSW) value determined based at least in part on the input; and a second neural network configured to receive the total soil water as an input, wherein the second neural network is configured to generate the crop yield based at least in part on the total soil water. Further, the system may include a decision support system for agrotechnology transfer (DSSAT) module configured to communicate with the cascading neural network over a network.

The first neural network may be configured to receive training data from the DSSAT module and train using the training data prior to generating the total soil water (TSW) value; and the second neural network is configured to receive training data from the DSSAT module and train using the training data before generating the crop yield. The at least one computing device may include a microcontroller implemented in a mobile irrigation machine; and the irrigation system may be instructed to apply irrigation to at least one crop in accordance with the optimal irrigation schedule by converting the optimal irrigation schedule to a suitable signal for interpretation by the irrigation system. The system may further include at least one soil moisture sensor positioned in the at least one region of the field, where the optimal irrigation schedule is determined based at least in part on a soil moisture measurement obtained by the at least one soil moisture sensor.

According to a second embodiment, a computer-implemented method for reinforcement learning-based irrigation control is described to maintain or increase a crop yield or reduce water use. The method includes determining, by at least one computing device, an optimal irrigation schedule for at least one crop in at least one region of a field by executing a reinforcement learning (RL) routine, where, for a given state of a total soil moisture, the reinforcement learning (RL) routine comprises: simulating, by the at least one computing device, an action, the action comprising waiting or irrigating the at least one crop; and assigning, by the at least one computing device, an immediate reward to a state-action pair, the state-action pair comprising the given state of the total soil moisture and the action performed; and instructing an irrigation system to apply irrigation to at least one crop in accordance with the optimal irrigation schedule determined, wherein the optimal irrigation schedule comprises an amount of water and a determined time at which the amount of water should be applied.

The optimal irrigation schedule may be determined using at least one of: a real-time soil moisture value, a near real-time soil moisture value, a predictive evapotranspiration (ET) metric, or a weather forecast metric. The method may further include generating, by a cascading neural network, a crop yield, wherein the crop yield is used to assign the immediate reward to the state-action pair. Generating, by the cascading neural network, the crop yield further may include: receiving, by a first neural network, as an input, at least one of irrigation data and weather data; providing, by the first neural network, a total soil water (TSW) value determined based at least in part on the input; receiving, by a second neural network, the total soil water as an input; and generating, by the second neural network, the crop yield based at least in part on the total soil water.

The method may further include receiving, by the first neural network, training data from a decision support system for agrotechnology transfer (DSSAT) module; training, by the first neural network, using the training data prior to generating the total soil water (TSW) value; receiving, by the second neural network, training data from the DSSAT module; and training, by the second neural network, using the training data prior to generating the crop yield. The at least one computing device may include a microcontroller implemented in a mobile irrigation machine, and the method may further include applying, by the microcontroller, irrigation to at least one crop in accordance with the optimal irrigation schedule by converting the optimal irrigation schedule to a suitable signal for interpretation by the irrigation system. The optimal irrigation schedule may be determined based at least in part on a soil moisture measurement obtained by at least one soil moisture sensor positioned in the at least one region of the field.

BRIEF DESCRIPTION OF THE DRAWINGS

Many aspects of the present disclosure can be better understood with reference to the following drawings. The components in the drawings are not necessarily to scale, with emphasis instead being placed upon clearly illustrating the principles of the disclosure. Moreover, in the drawings, like reference numerals designate corresponding parts throughout the several views.

FIG. 7 is an example of the SARSA($\lambda$) algorithm implemented in an irrigation control application according to various embodiments of the present disclosure.

DETAILED DESCRIPTION

Figure 1:
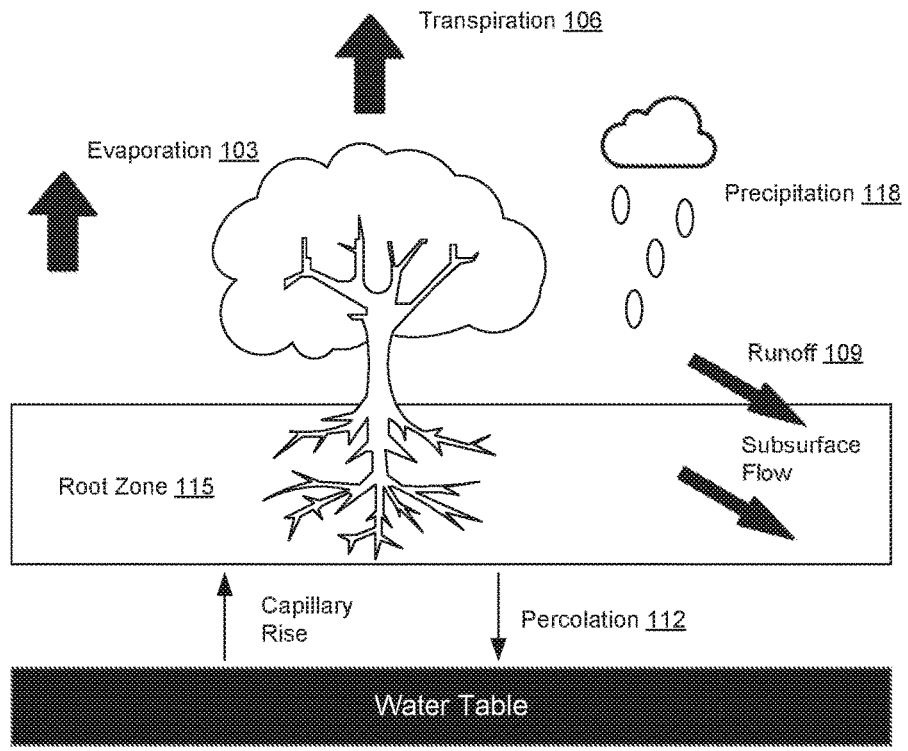
FIG. 1 is a drawing showing factors of water gain and loss in soil.

According to various embodiments of the present disclosure, a system may include at least one computing device having a controller application configured to implement a reinforcement learning (RL) routine in an irrigation control system that makes use of soil moisture sensor and weather information. The controller application may be implemented in or otherwise integrated with an irrigation system, such as a center pivot irrigation machine, a lawn irrigation system, or a drip irrigation system, as will be discussed.

In reinforcement learning, a key element is the reward function, which tells if an action is generally good or poor. For agricultural irrigation, the critical reward—crop yield, is not known until the end of a crop season. Such delayed reward may be handled by implementing a temporal difference approach in reinforcement learning. For instance, due to limited real data, offline learning through simulation may be applied. To this end, fast models based on neural networks are developed to facilitate scalable learning. The embodiments described herein are simulated by a fast model developed upon the Decision Support System for Agrotechnology Transfer (DSSAT) module, which includes a model for crop growth.

According to various embodiments, a control application may be executed in at least one computing device to determine an optimal irrigation schedule that includes an amount of irrigation (e.g., water) to apply as well as a time at when to apply the irrigation. The optimal irrigation schedule may be determined using various artificial intelligence techniques, including reinforcement learning, and may be implemented in a mobile or static irrigation system. The control application maintains or increases crop yield while decreasing water usage. In order to do so, the control application may utilize real-time soil moisture sensor data provided, for example, wirelessly, from soil moisture sensors positioned throughout a crop field. Further, the control application may utilize evapotranspiration (ET) values obtained from the National Digital Forecast Database (NDFD) and/or a local weather station, which may involve application programming interface (API) made available over a network, such as the Internet. When implementing embodiments of the systems and methods described herein, a 20% water use reduction while maintaining a same crop yield is observed when compared to previous methods. As such, the embodiments described herein are directed towards technological improvements in computer-based irrigation systems that improve the overall operation of irrigation in an agricultural, landscape, or similar environment. Further, the embodiments described herein provide an optimized tradeoff between the use of computing resources and a desired degree of accuracy of predictions.

Further, the control application described herein may run analyses based on future weather, and may handle situations where outcomes, like precipitation and soil moisture level, are random while partially depending on the control of the operator. Notably, the control application may save a substantial amount of water by calculating the best option of whether to irrigate a certain amount of water or wait.

Turning now to the drawings, FIG. 1 includes a drawing that shows a variety of factors for water gain and loss in soil. To implement a reinforcement learning routine, a control application may model an irrigation decision-making process as an optimization problem in a stochastic system. As may be appreciated, soil moisture levels drop due to evaporation 103, transpiration 106, runoff 109, and percolation 112. When rainfall is insufficient, irrigation may be applied to provide soil moisture to meet crop needs. Several irrigation applications are usually needed during an entire crop season. Traditionally, an irrigation schedule is set to periodic applications (calendar-based schedule) or may be triggered by a certain threshold (e.g., when soil moisture reaches a depletion level). For instance, whenever a soil moisture level drops below a predefined threshold, the control application may cause an irrigation machine to irrigate one or more areas of a field until the field is replenished to a target filling point (TFP). The conventional irrigation scheduling or control strategies do not consider forecasted in-season rainfall; hence, often the rainfall is not fully utilized and water is wasted through over-irrigation, thereby resulting in runoff and deep percolation.

Figure 2:
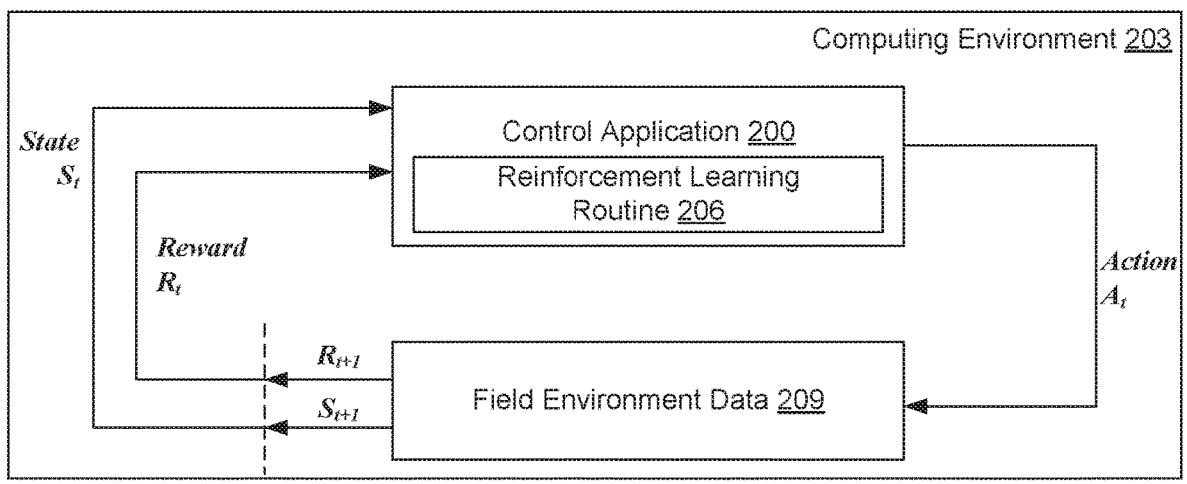
FIG. 2 is an example of a control application configured to employ reinforcement learning to optimize water usage and a crop yield according to various embodiments of the present disclosure.

Turning now to FIG. 2, a control application 200 is shown executing in a computing environment 203. The computing environment 203 may include a remote computing environment 203 that communicates with devices and services through a network, such as the Internet or other telecommunications network. When network communication is made available through the Internet and/or other networks, irrigation control may further incorporate weather conditions and weather forecast information received from a suitable weather service (e.g., a web service application programming interface). The network may include, for example, the Internet, intranets, extranets, wide area networks (WANs), local area networks (LANs), wired networks, wireless networks, or other suitable networks, etc., or any combination of two or more such networks. For example, such networks may comprise satellite networks, cable networks, Ethernet networks, and other types of networks.

The computing environment 103 may comprise, for example, a server computer, a microcontroller, or any other system providing computing capability. Alternatively, the computing environment 103 may employ a plurality of computing devices that may be arranged, for example, in one or more server banks or computer banks or other arrangements. Such computing devices may be located in a single installation or may be distributed among many different geographical locations. For example, the computing environment 103 may include a plurality of computing devices that together may comprise a hosted computing resource, a grid computing resource, and/or any other distributed computing arrangement. In some cases, the computing environment 103 may correspond to an elastic computing resource where the allotted capacity of processing, network, storage, or other computing-related resources may vary over time.

The control application 200 may model the cost of taking any action and consequence of being at any state in a form similar to the Bellmen equation. A state s, may include a state of a crop field, where the state may include a soil moisture level. The control application 200 may identify a set of actions to perform, such as waiting (e.g., doing nothing) or irrigating (applying water to the field) based on the state of the field s. As such, the control application 200 may determine whether to wait or irrigate the field to one of N levels. The control application 200 may further utilize a transition function T(s, a, s'), which may be affected by both the action, future precipitation, and evapotranspiration loss. In some embodiments, the transition function may include a function of evapotranspiration and weather forecast data. A reward function R (s, a, s') may include an amount of water, but multiplied by −1. A utility metric may include the sum of (discounted) rewards, where V*(s) is an expected utility starting in s and acting optimally while Q*(s,a) is an expected utility starting out having taken action a from state s and thereafter acting optimally.

In various embodiments, the control application 200 may evenly divide the soil moisture value between the permanent wilting point (PWP) and the field capacity by N different levels. The difference between adjacent levels may be determined by a desired precision of an irrigation system. An allowable depletion level (e.g., a metric defined by an operator or an administrator) may include a soil moisture level between the permanent wilting point and the field capacity, and may indicate a maximum amount of plant available water (PAW) allowed to be removed from the soil before irrigation occurs to prevent crop drought stress.

Each level of soil moisture may be defined as a state s, which describes the status of the measured field. A large N value may be used to provide a more accurate and efficient control. However, in reality, tuning of an irrigation system cannot be infinitely accurate. Thus, dividing the soil moisture level beyond irrigation resolution may not assist in increasing the efficiency of overall water usage. Additionally, increasing the number of N requires more computational resources. Therefore, N may be set to a value between ten and twenty to provide a good balance between water efficiency and computational capacity of an irrigation controller. The actions may include a response (or an action) that may be performed by the irrigation system according to current situation. Actions may include predefined events stored in memory of the computing environment 203. In some examples, actions include irrigating, abstaining from irrigating, etc. The action may be selected from one of the predefined events stored in memory by the control application 200 in order to maximize the accumulated reward over a predictable period. A reward function may be formulated to provide an ultimate goal of maintaining (or even increasing) crop yield while saving water.

Transitions between states may partly depend on actions taken, and are probabilistic. For instance, transitions may also depend on weather, especially precipitation. A transition matrix may include an N×N matrix that describes odds for each state pairs. The control application 200 may generate the transition matrix by the latest twenty-four to seventy-two hours (or longer) quantitative precipitation forecast (QPF). The choice of the length of quantitative precipitation forecast may be related to the speed of water infiltration, the volumetric rate of water provided to the system, and the availability of quantitative precipitation forecast. Normally, it takes twelve to twenty-four hours for water to reach major root area or depth capable of being measured by soil moisture sensors. Thus, in some embodiments, quantitative precipitation forecasts are utilized by the control application 200 that are longer than twelve hours, as any immediate irrigation is not only unnecessary, but also potentially inaccurate. The longer the predictable time length, the more efficiently the control application 200 may operate.

For example, if a large precipitation were to happen in one day, the control application 200 using twenty-four hours of quantitative precipitation forecast would be able to determine that it is better to irrigate a smaller amount of water or even abstain from irrigating the field (depending on different soil moisture level) as long as the risk of dropping below the lower soil moisture threshold is acceptable. However, if rain might occur in three days, then the control application 200 using twenty-four hours of quantitative precipitation forecast might not be informed. Instead, it would just irrigate to the field capacity. In this case, when it rains three days later, much of the water could be wasted.

On the other hand, if the control application 200 uses seventy-two hours of quantitative precipitation forecast, then the control application 200 may be required to iterate through every possible scenario and make an optimal choice which may include, for example, waiting, irrigating a limited amount, or more fully utilizing rain to refill the soil with water. Quantitative precipitation forecast may come in two different forms, for example. First, the quantitative precipitation forecast may include a probability density function, which shows a probability of different amounts of precipitation. Second, the quantitative precipitation forecast may include an expected value. For example, the expected value may include a weighted average of all possible outcomes. The control application 200 may form a transition matrix from the quantitative precipitation forecast according a water balance equation:

$$SML(k+1)=SML(k)-ET(k+1)+P(k+1)+I(k) \quad \text{(eq. 1)},$$

where SML(k) indicates soil moisture level at time step k. Since SML(k), ET(k), I(k) are deterministic, the distribution of SML(k+1) is in the same shape with P(k+1). If the control application 200, for instance, at the direction of the operator, implements a seventy-two hours weather forecast, then once the control application 200 downloads weather forecast data, the control application 200 may generate 3*N different transition matrix for each of the following day and action pair. The design of the reward function R(s, a, s') is based on saving water and maintaining soil moisture level above a minimum threshold.

Given a state, if the control application 200 chooses to wait, then the immediate reward may be zero as waiting doesn't cost anything. On the other hand, if the control application 200 chooses to fill the soil to the field capacity, then, based on evapotranspiration and quantitative precipitation forecast, the control application 200 may generate a needed water amount and use it to represent the cost for each state-action pair. As the control application 200 is attempting to lower cost by saving water, the reward value is negative. The reward function may only represent the immediate water cost, yet it does not carry any information about the long-term effect of being at certain state.

Thus, V*(s) may model the risk and benefit of being at a state s. Because excessive soil moisture can impede root development, limit oxygen in the root zone, and cause leaching of soil nutrients, it is not ideal to have excessive moisture in the soil. Thus, moisture levels above field capacity are discouraged. As such, the control application 200 may assign negative values according to the level above field capacity. Also, the soil moisture level should not drop below the lower soil water threshold (at which crop stress occurs), and should never drop to permanent wilting point as the crop will die. Hence, a substantially negative value may be assigned to those levels near the lower soil water threshold or PWP. An example of V values may appear as follows:

$$V(s)=[-0.005,-0.004,-0.003,-0.002,-0.001,0.005,-10,-10]$$

The Bellmen equation may be utilized to find an optimal action for each given state at a given day:

$$\max(a)\Sigma(s')T(s,a,s')[R(s,a,s')+\gamma V^*(s')] \quad \text{(eq. 2)},$$

where γ, having a value between 0 and 1, is a discount factor. T(s, a, s') and R(s,a) may be used for each state-action pair, for instance, to calculate the utility values for each action such that the control application 200 may pick the one that leads to maximum utility value. When the soil moisture level is within healthy range, and there is no immediate risk of running below the lower threshold, the control application 200 may determine that is better to wait rather than fill the soil to field capacity.

As may be appreciated, the control application 200 may make a different choice if the situation changes. For instance, the current soil moisture level may be near the lower threshold, and the expected precipitation the next day may not refill soil moisture above the threshold. Without irrigation, crop drought stress or death might occur. Accordingly, after calculation, the control application 200 may determine that waiting to irrigate will incur a much larger loss compared to incurring the water cost by irrigating. Thus, the optimized irrigation schedule may include irrigating the field.

Referring again to FIG. 1, a schematic diagram is shown that illustrates a variety of factors for water gain and loss in soil. As may be appreciated, an amount of water in soil varies over time depending on many factors. Notably, there are five ways of water loss and two ways of water gain. Due to gravity (e.g., drainage), water retained in soil is pulled out of a root zone 115 to deeper layers, where the loss may be referred to as "deep" percolation 112. Evapotranspiration includes a combination of transpiration 106 and evaporation 103. Evapotranspiration accounts for plant water use (transpiration 106) and water evaporated from the soil and wet surfaces (evaporation 103). Water applied at rates exceeding an intake capacity of soil may be lost through runoff 109.

In arid and semi-arid areas, insufficient availability of water in the crop root zone 115 often is the primary limiting factor for crop yield. Even in relatively humid environments, seasonal or occasional drought conditions can result in water-limiting growing conditions, requiring irrigation (e.g., water) to be applied to protect against a loss in crop yield. To show the importance of irrigation, DSSAT simulations of maize growth in Temple, Tex. according to the weather of 1984 may be performed for different irrigation scenarios. The DSSAT simulations may compare crop yield, for instance, when a crop does not receive irrigation to a range of different amounts of water profiles in soil. For instance, scenarios of different amounts of irrigation may include twenty millimeters (mm) of water over ten days, thirty millimeters of water over ten days, and forty millimeters of water over ten days.

Referring again to FIG. 2, the control application 200 executing in a computing environment 203 may implement a reinforcement learning (RL) routine 206. The control application 200 and the reinforcement learning routine 206 may include program instructions executable in at least one computing device that, when executed, directs the control application 200 to determine an optimal irrigation schedule for at least one crop in at least one region of a field by executing the reinforcement learning routine 206. In some examples, the reinforcement learning routine 206 includes the Deep-Q learning routine, the A3C learning routine, or other suitable learning routine 206.

For a given state of a total soil moisture, the control application 200 may perform an action, such as waiting or irrigating at least one crop. The control application 200 may assign an immediate reward to a state-action pair, where the state-action pair includes the given state of the total soil moisture and the action performed, as will be discussed. Further, the control application 200 may instruct an irrigation system to apply irrigation to at least one crop in accordance with the optimal irrigation schedule determined, where the optimal irrigation schedule includes an amount of water to be applied at a predetermined time.

As noted above, the control application 200 may determine the optimal irrigation schedule using field environment data 209, which may be received over a network and/or accessed from memory of the computing environment 203. In various embodiments, the field environment data 209 includes real-time soil moisture values, near real-time and/or predictive evapotranspiration, and weather forecast data. Additionally, the control application 200 may utilize a system for agrotechnology transfer module, as well as cascading neural networks, as will be discussed. In some embodiments, the control application 200 may be is implemented in a mobile irrigation machine.

Figure 3:
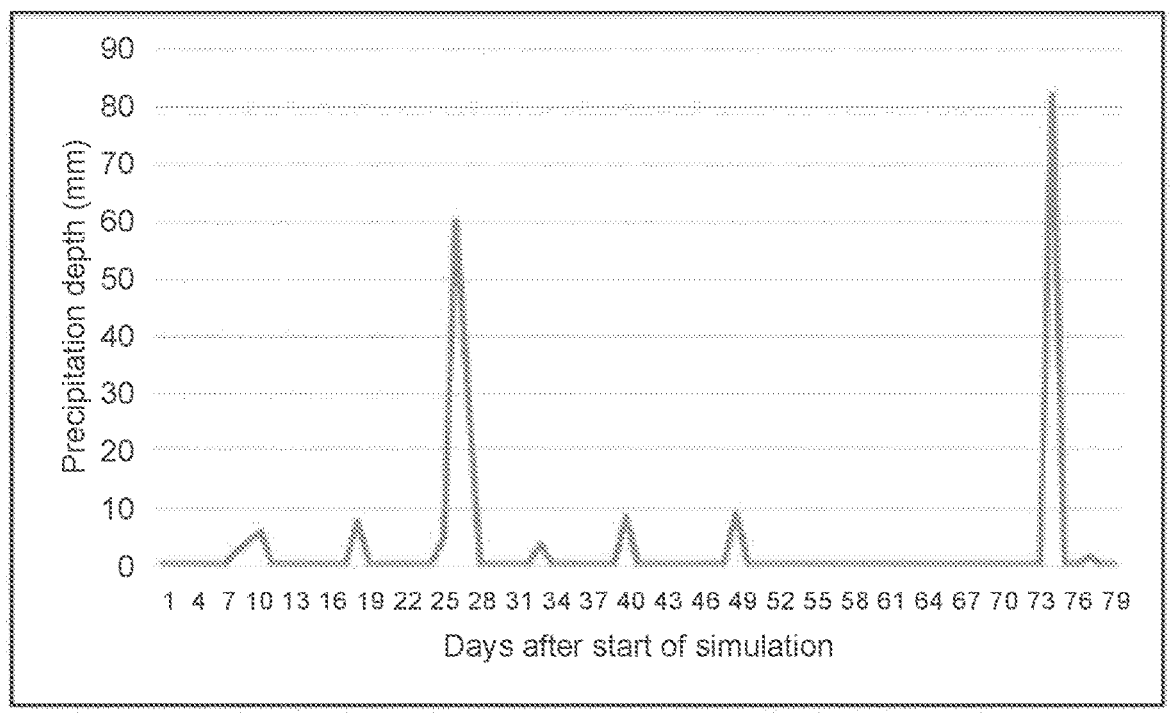
FIG. 3 is a graph showing precipitation during a simulated crop season.
Figure 4:
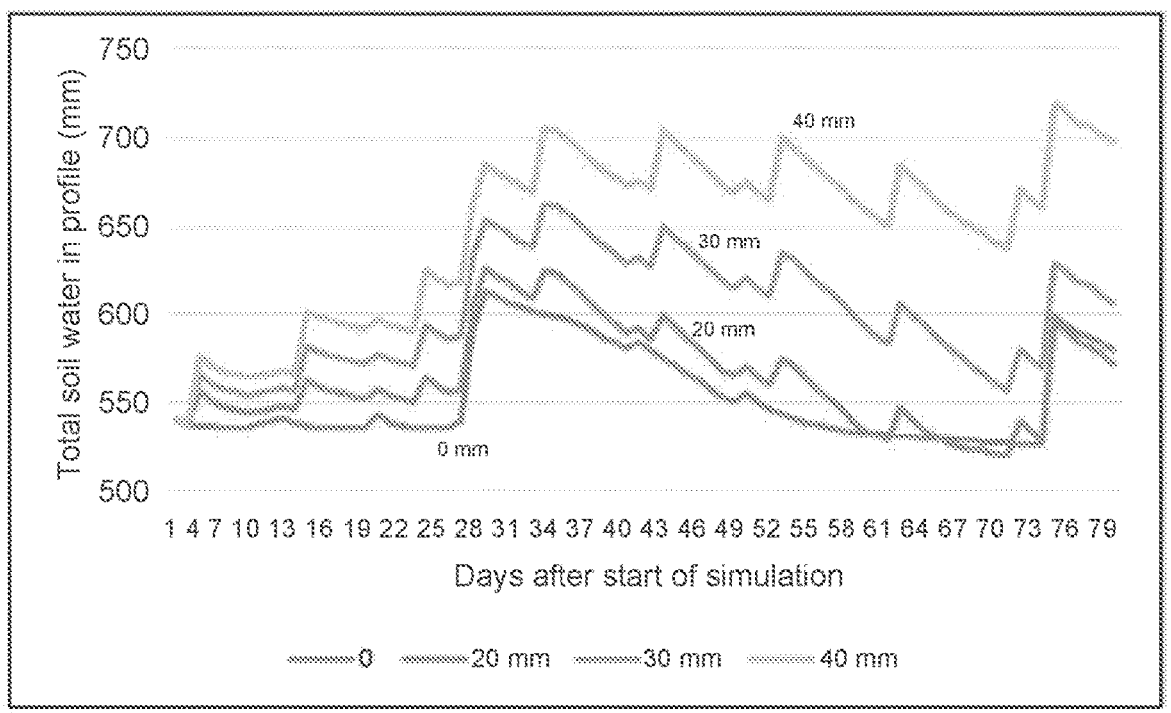
FIG. 4 is a graph showing total soil water in a soil profile during a simulated crop season.

Precipitation 118 observed over a period of seventy-nine days is shown in a graph of FIG. 3. FIG. 3 shows precipitation depth during a period of a simulated crop season having a total amount of rainfall of 219 mm. The variation of total water in the profile is depicted in a graph shown in FIG. 3. FIG. 4 shows a total soil water in a profile during the period of simulated crop season. The notable increase observed at day twenty-six is caused by a storm on day twenty-five. Without a sufficient amount of water, the total soil water drops below 540 mm for 21 days until the end of the crop season when it rains on day seventy-four. Differences in the crop yield in the simulation can be observed from Table 1 below:

TABLE 1

Comparison of Yield under Different Irrigation Plans

| | Irrigation Plan (mm/10 days) | | | |
|---|---|---|---|---|
| | 0 | 20 | 30 | 40 |
| Yield (kg/ha) | 2262 | 6257 | 6880 | 6305 |

From Table 1, it can be easily determined that irrigation makes a substantial difference in crop yield. Under the twenty millimeters over ten days simulation, with 160 mm of water supplied in total, the crop yield is increased by 176.6% when compared to no irrigation. However, irrigation does not necessarily increase crop yield. When comparing the yield under twenty, thirty, and forty millimeters over ten days, one can see that an additional ten millimeters of water above twenty can boost the crop yield by an additional 10%. However, a further increase of the water supply to forty millimeters actually suppresses the yield by 8%.

Water requirements vary by crop and growth stage. For example, excess water at a germination stage can cause poor aeration and discourage proper root development. Supplying a crop with a right amount of water at a specific time becomes increasingly important (as well as practically achievable) in modern agriculture. As may be appreciated, the most suitable amount of water and a most suitable time to apply the water to a crop are very difficult to determine in traditional practice, as farmers most commonly use fixed interval irrigation scheduling. As such, the flexibility and precision required to adjust for precipitation and soil water balance is non-existent, and a risk of over-watering a crop (e.g., wasting water) or under-watering the crop leading to yield losses is apparent.

In some embodiments described herein, a system may include the computing environment 203 and a plurality of soil moisture sensors positioned in various regions of a field to observe soil moisture for a crop or other item planted in the field. While soil moisture sensors may be positioned throughout a field and irrigation applied when a soil water value drops below a threshold, the question of how much water to apply to a crop is traditionally not well answered. Traditionally, a fixed amount of water is applied at a constant frequency. Some irrigation management technologies exist; however, their use in agriculture evolved along two orthogonal directions. For instance, advanced algorithms for optimizing problem sets have evolved independently of utilization of modern hardware technology, such as wireless sensors and wireless sensor networks. However, neither solution addresses uncertainties in soil, crop, and weather conditions. Most techniques were developed before the advent of wireless sensor technology, and therefore, these techniques are highly dependent on the accuracy of models, which are not reliable.

The control application 200 may model a growth process for a particular crop as a Markov chain, which includes a model for probabilistic transitions among a set of states $S=\{s_1, s_2, \ldots\}$ over time. In agricultural irrigation, each state $s_i \in S$ may be defined as a total soil water (TSW) level at a certain crop growth stage. Depending on specific types of crop and soil, a minimum soil moisture level (management allowable depletion threshold) will be set higher than the permanent wilting point (PWP), at which plants can no longer extract water from soil (and potentially die). A time step may include three days, although the time step may be tuned to other values.

An irrigation decision (e.g., a decision whether to irrigate a crop) is made from a set of actions $A=\{a_1, a_2, \ldots\}$ stored in memory defined as irrigating the soil until a designated target filling point (TPF) is reached. A decision of which action to take directly may affect the state that can be reached at a next time step. Therefore, the control application 200 may implement a Markov decision process (MDP).

In a Markov decision process, an action $a_j \in A$ at a certain state $s_i \varepsilon S$ leads to an immediate reward $r(s_i, a_j)$. The strategy of choosing actions at each time step may be summarized as a policy, which usually aims to maximize a long term return or cumulative reward. In agricultural irrigation, the long term return may be defined as a Net Return where the Net Return may be determined using the following equation:

$$\text{NetReturn}=Y^*P_y-C^*P_c \quad \text{(eq. 3)},$$

where Y is a crop yield with a unit of kilograms (kg) per harvest (ha) (kg/ha), C is water usage with a unit of ha-mm/ha, $P_y$, and $P_c$ is a product and water price with a unit of dollars/kg and dollars/mm, respectively. Contrasting with previous methods, embodiments of the present disclosure do not merely optimize water use or crop yield; rather, the optimization of a net return is optimized. For instance, farmers or other individuals may use embodiments of the present disclosure to determine a direct measurement of economic gain, and are able to adjust the strategy according to a future market and future water price.

To derive a policy for a Markov decision process, one of several methods may be employed. In various embodiments of the present disclosure, the control application 200 executing in the computing environment 203 is configured to implement model-free reinforcement learning. Namely, the model-free reinforcement learning does not depend on an assumption or prior knowledge, but instead acquires experience by interacting with an environment.

For instance, at each time step, the control application 200 may take an action $a \in A$ depending on a current state $s \in S$, and observe an immediate reward r. At the next time step, the previous reward r may be discounted by a factor, whose value may be between zero and one. The factor may control the preference of behavior for the control application 200. For instance, when the factor is equal to one, the control application 200 would implement a long-term strategy. Alternatively, if the factor were equal to zero, the control application 200 would only strive for a large immediate reward. The quality of a state-action pair is specified by a function Q(s,a), which defines an expected cumulative reward by being at state s and taking action a.

The value of the function is largely decided by a reward resulting from a trajectory of state-action pairs. A challenge in irrigation is that crop yield, the critical reward, is not known until the end of the crop season. Thus, in some embodiments, a temporal difference learning algorithm, such as SARSA(λ), may be utilized to account for a delayed reward. Notably, SARSA(λ) updates Q-functions for state-action pairs backwards in accordance with an eligibility trace, in which λ controls an eligibility (or a relevance of a later reward to previous state-action pairs). A Q-function is a function that determines probability that a normal (Gaussian) random variable will obtain a value larger than x standard deviations above the mean. Equivalently, the Q-function, Q(x), is the probability that a standard normal random variable takes a value larger than x.

A common issue faced by reinforcement learning is a trade-off between exploitation and exploration. Specifically, the control application 200 may explore an environment and learn from experience. However, at early stages, heavily relying on learned Q-values or exploitation to make decisions may reduce any opportunity to discover improved routes. At later stages, it may be wasteful to spend too much time on exploration rather than using existing knowledge. Thus, the exploitation-exploration trade-off may be addressed utilizing the ϵ-greedy algorithm, where an action with a largest Q-value is taken with a probability of 1−ϵ and an action is randomly chosen among all actions with probability E. At state s, action a may be taken according to the ϵ-greedy algorithm. Then, a reward r may be received and the state transitions to s'. Let a' be the next action according to the ϵ-greedy algorithm. The Q-value of the state-action pair (s', a') may be updated with a temporal difference (δ) defined using the following equation:

$$\delta = r + \gamma Q(s', a') - Q(s, a) \quad \text{(eq. 4)}$$

The control application 200 may maintain a record of the eligibility trace e(s,a) in memory. After each visit, the eligibility value of a current state-action pair may be incremented by one:

$$e(s,a) \leftarrow e(s,a) + 1 \quad \text{(eq. 5)}.$$

After each visit, all entries of the Q-table may be updated according to the temporal difference (δ) and e(s,a) with a learning rate α:

$$Q(s,a) \leftarrow Q(s,a) + \alpha \delta e(s,a) \quad \text{(eq. 6)}.$$

The eligibility may be discounted by the product of γ and λ so that rewards obtained at later time steps are updated according to a relevance of a previous state-action pair. The longer a distance, the smaller a relevance, and, therefore, less weights on the updates:

$$e(s,a) \leftarrow \gamma \lambda e(s,a) \quad \text{(eq. 7)}.$$

The above process may be repeated until either the Q-table is converged or the policy is sufficiently stabilized. Notably, the process includes both learning and decision making.

In order to learn what is good and bad in terms of policy, the control application 200 may interact with an environment. However, the process may be slow as learning from one actual crop season may take ninety to 120 days depending on a type of crop and a time of planting. Thus, to shorten the learning process, simulation modules, such as the DSSAT module, may be utilized. However, directly incorporating the DSSAT module can be very difficult, as control of irrigation scheduling may require either manual editing through a graphical user interface (GUI) of the DSSAT module or understanding its source code written in Fortran.

Figures 5, 6:
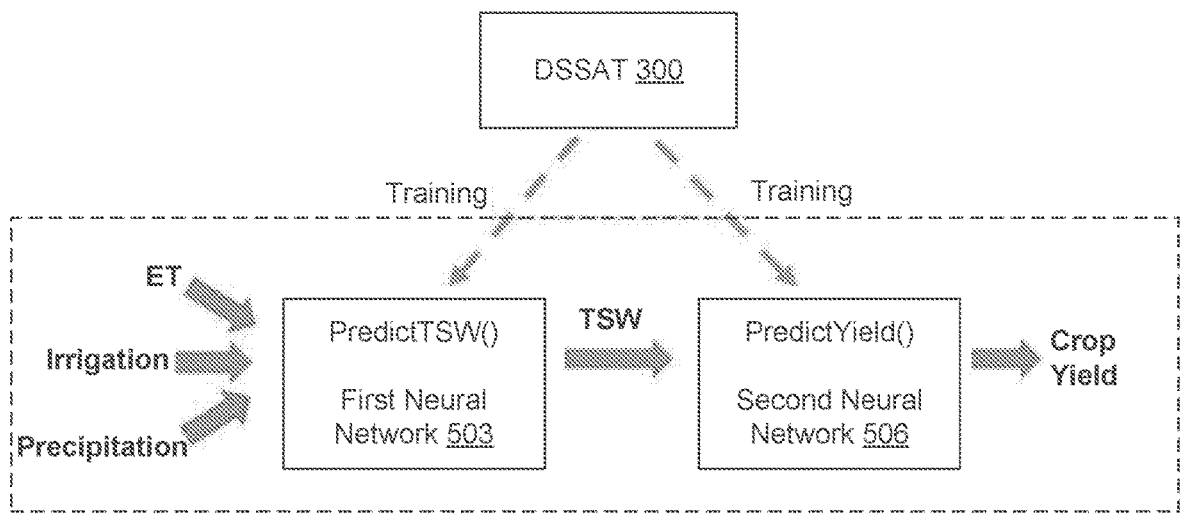
FIG. 5 is a schematic diagram showing a process to construct cascading neural networks for simulation of total soil water level and crop yield using DSSAT model according to various embodiments of the present disclosure.
FIG. 6 is an example of an algorithm for generating a daily total soil water and irrigation record according to various embodiments of the present disclosure.
Figure 8:
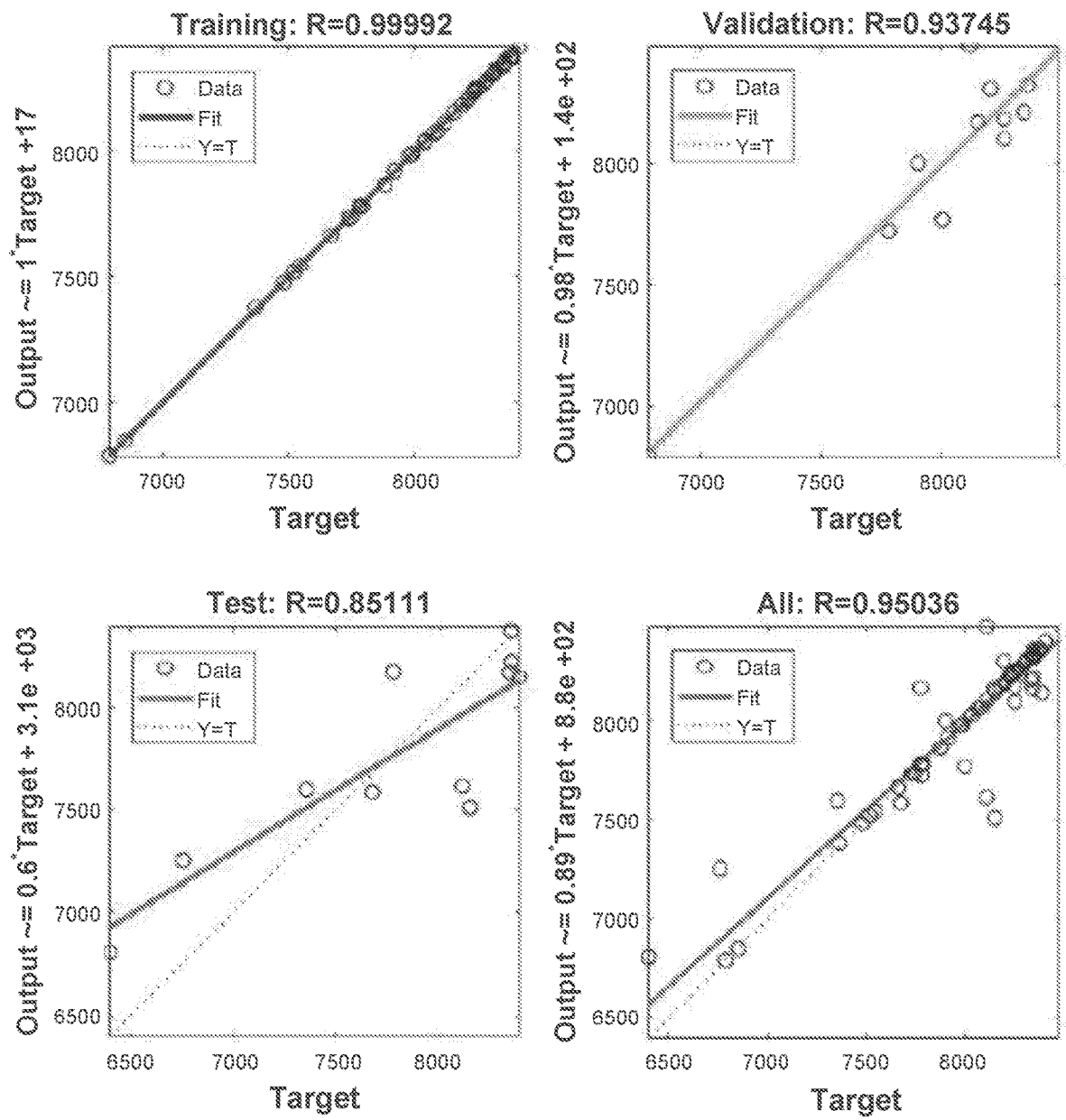
FIG. 8 is a graph illustrating a neural network training regression for predicting yield according to various embodiments of the present disclosure.
Figure 9:
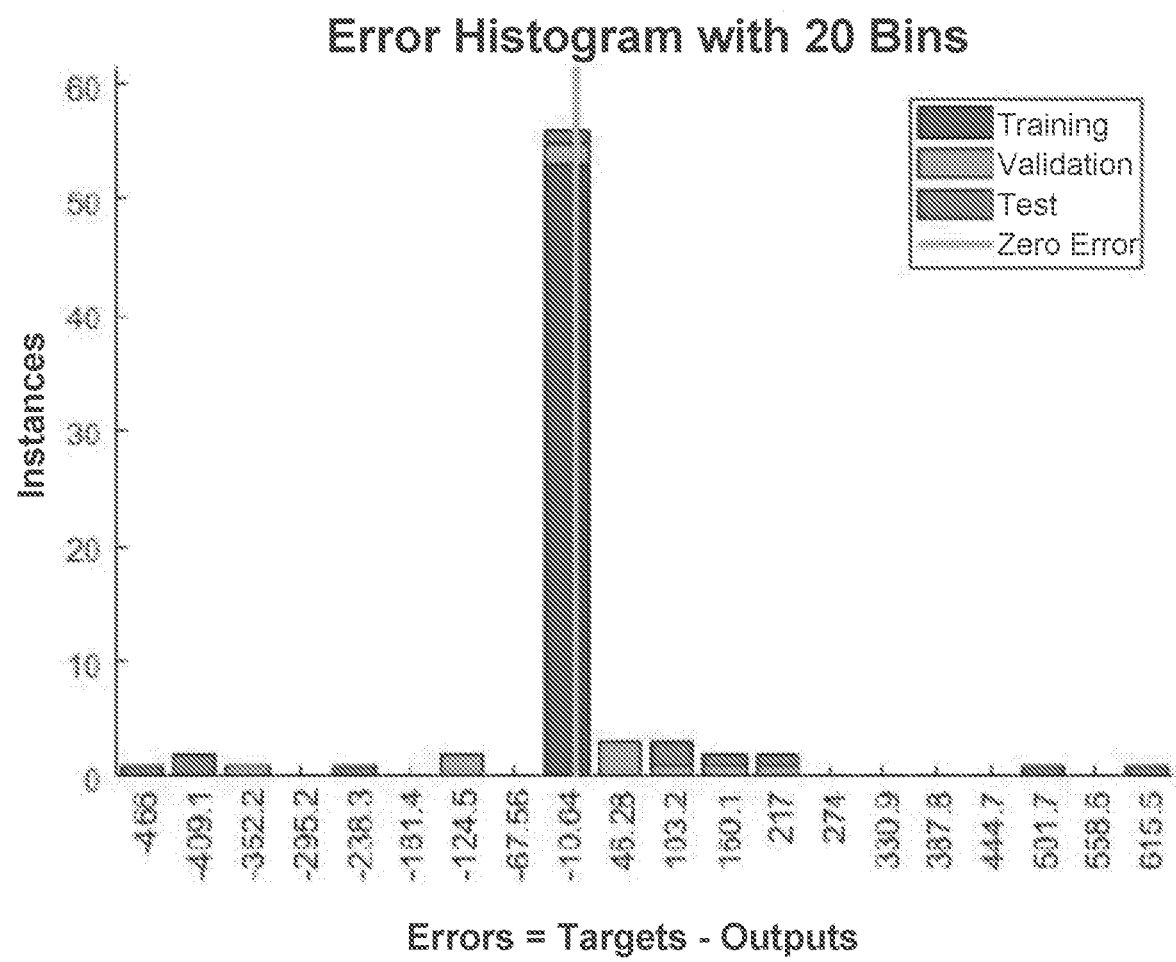
FIG. 9 is an error histogram illustrating neural network training error for predicting yield according to various embodiments of the present disclosure.
Figure 10:
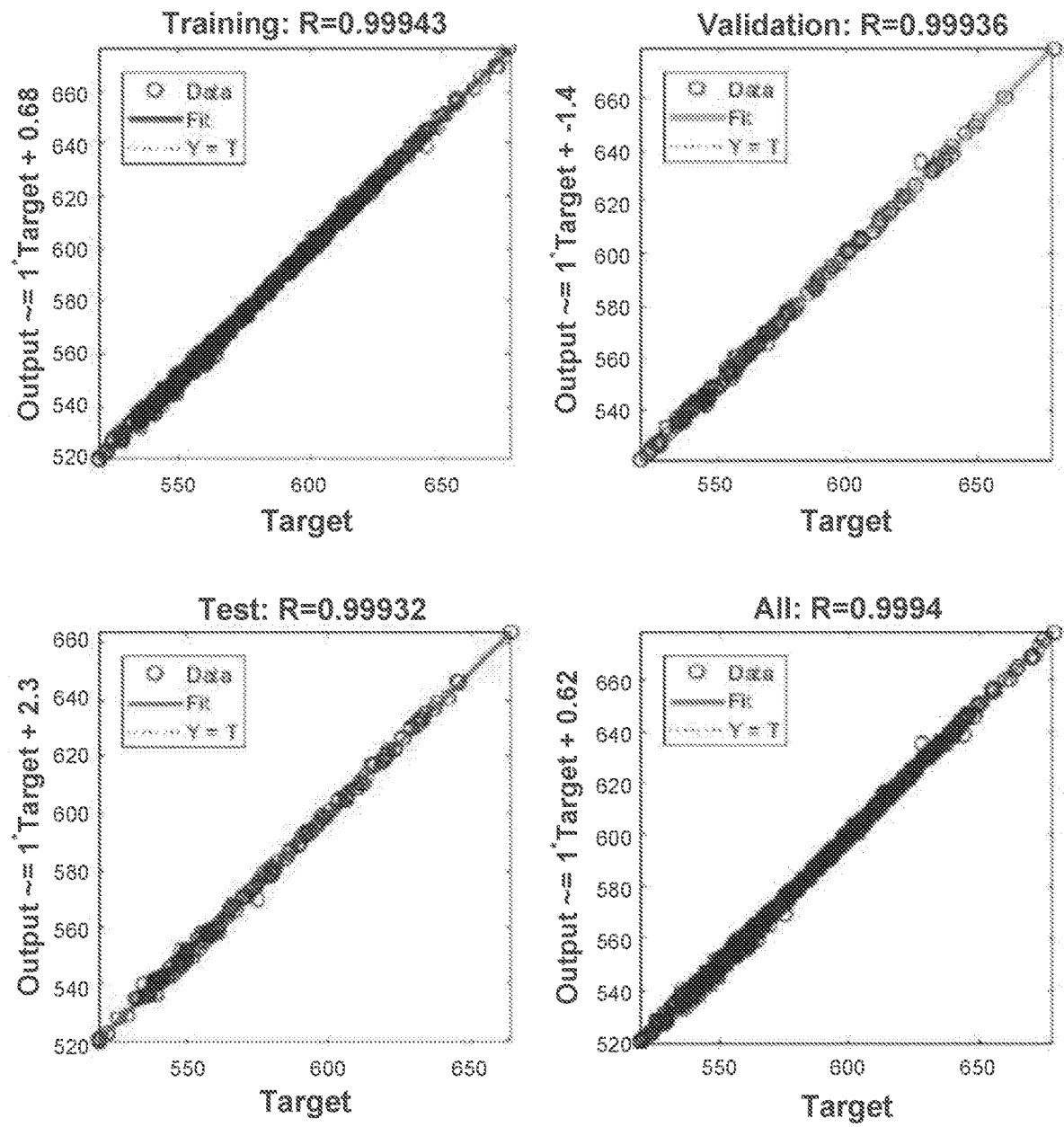
FIG. 10 is a graph illustrating a neural network training regression for predicting total soil water level according to various embodiments of the present disclosure.
Figure 11:
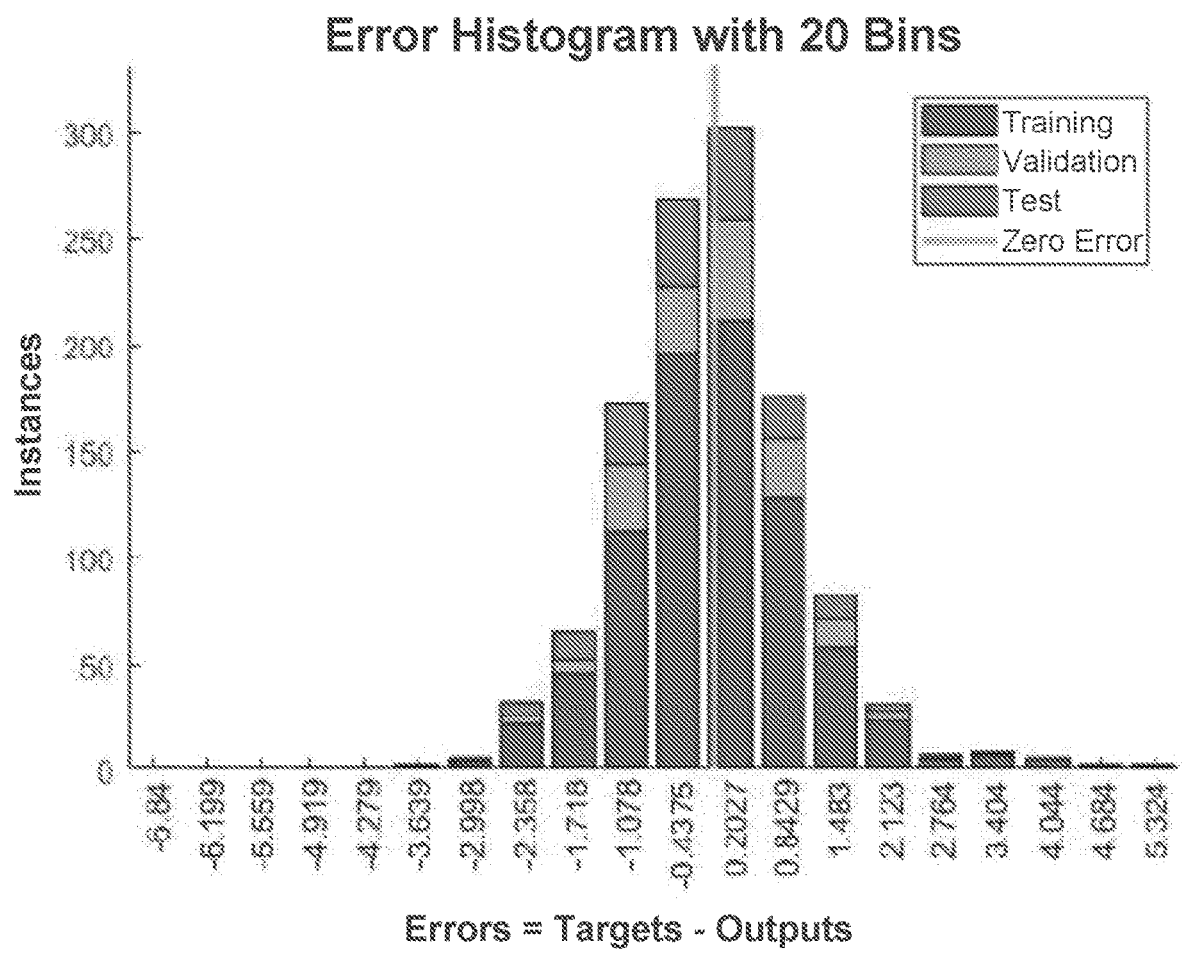
FIG. 11 is an error histogram illustrating neural network training error for predicting total soil water level according to various embodiments of the present disclosure.

Referring now to FIG. 5, to make Q-function training more scalable, cascading neural networks (NNs) may be used in accordance with some embodiments as a surrogate to the DSSAT module. For instance, the cascading neural networks (NNs) may include a first neural network 503 that accepts irrigation and weather information (e.g., ET and precipitation) as inputs and predicts a total soil water ("PredictTSW( )") for a geographic location, as shown in FIG. 5. Additionally, a second neural network 506 may be utilized, where the second neural network 506 may predict crop yield ("PredictYield( )") given the daily total soil water of an entire crop season determined by the first neural network 503. Since a final crop yield may be closely related to total soil water during a simulated crop season, random irrigation plans may be run and total water soil tables may be used as inputs, and crop yields obtained may be used as targets to train the second neural network 506 that ultimately determines crop yield.

As shown in FIG. 5, the input to the second neural network 506 may include the output of the first neural network 503 that is configured to predict a daily total soil water. The total soil water level may be affected by not only precipitation and irrigation, but also ET, runoff, and percolation, which themselves vary as a function of soil type, solar radiation, wind speed, temperatures, etc. In the DSSAT module, the total soil water may be calculated and data obtained from simulations ran by the DSSAT module may be used to train the first neural network.

In the SARSA(λ) algorithm, although each time step may be three days, a prediction of crop yield may require total soil water data daily. As described in an algorithm shown in FIG. 6, the control application 200 may first translate time step i to days [j,j+2]. Then, the control application 200 may calculate an irrigation water depth $I_j$ for day j according to a current TSW ($TSW_j$), and a target filling point (TFP) may be decided by actions in A using a function IrrigationAmount( ). Because frequent small irrigation applications can result in a large evaporation loss and discourage deep root development, the depth of any irrigation application may be required to be at least a certain amount, (such as twenty millimeters) depending upon local soil conditions. Once the amount is determined, the control application 200 may run the neural network function PredTSW( ) to produce TSW values for the following three days. The function may accept, as its parameters, a current TSW, irrigation (if any), ET, and precipitation.

The reward function design for the SARSA(λ) learning in irrigation warrants particular discussion. A long term return may include the net return resulting from crop yield and water expense. Since water application occurs multiple times throughout a crop season, one embodiment may include counting a water use expense immediately after each irrigation action. However, this approach incurs two problems. First, a reward due to water use is negative (e.g., a punishment) as water use should be minimized instead of being maximized. A negative reward often results in negative Q-values, which interferes in the exploitation-exploration tradeoff. More specifically, a good action a* may temporarily have a negative Q-value, while another under-explored action a' may have a zero Q-value even though it is a poor action. The discrepancy may mislead the subsequent learning process.

Second, a reward may be discounted by eligibility trace in the SARSA(λ) learning. As such, a same dollar amount for water use and crop yield may be treated with different weights. To overcome these problems, the reward associated with water use may be deferred until the end of crop season. In other words, all time steps in the middle of a season have an immediate reward of zero. At the end of the season, there is only a single reward: the net return.

An algorithm for a learning process is shown in FIG. 7. Each simulated crop season may be referred to as an episode consisting of n time steps. The control application 200 may start with a pseudorandomly generated Q-table, where Q-values of all state-action pairs may be relatively small in magnitude as compared to rewards. At each time step, the control application 200 may take an action and run a function SimuTSW( ) to obtain total soil water and irrigation which may be recorded for the current time step. The reward function may be configured such that all immediate rewards are zero, except for the last reward. The final reward may include a net return, calculated by eq. 3. Notably, if a net return is smaller than a desired value threshold, then it may be assigned a small negative value, such as −50. Thus, good policy may be clearly distinguished from bad policy. A small negative value may also direct the control application 200 to favor other unexplored state-action pairs, thus making it faster to find good policies (e.g., increasing the speed of the computations). The control application 200 may update the Q-table and eligibility trace in memory at the end of each time step. Upon completion of each episode, the eligibility may be reset to, for example, all zeros; however, the Q-table may be kept as a reference to continue learning until convergence.

To evaluate effectiveness of the embodiments described herein, computer simulations were run on four different locations, as shown in Table 2, namely Temple, Tex., United States; Kununurra, Australia; Hyderabad, India; and Saskatchewan, Canada. In the computer simulations, the first three fields were planted with maize, and the last field was planted with wheat. The test cases are summarized in Table 2, below:

TABLE 2

General Information of Test Cases

| | Location | | | |
|---|---|---|---|---|
| | Temple | Kununurra | Hyderabad | Saskatchewan |
| Soil Type | Clay | Clay | Clay | Loam |
| Cultivar | Maize | Maize | Maize | Wheat |
| Planting Data | May 12, 1984 | Jun. 12, 1982 | May 12, 1983 | May 25, 1975 |

The neural networks for predicting total soil water and crop yield may be trained with a single hidden layer consisting of ten or other suitable amount of neurons. The training algorithm may include, for example, Levenberg-Marquardt. Samples may be divided into training, validation, and testing sets. The neural networks may be trained on training sets and validated by validation sets, which are used to instruct the neural networks to stop training. The accuracy of the neural networks may be measured on the test sets to provide unbiased results. FIGS. 6-9 demonstrate the training performance for the Temple case. Regression measures the correlation between targets and outputs, where values closer to one are better. In the error histogram of FIG. 9, the smaller and more concentrated around zero, the more accurate. The statistics of all test cases are summarized in Table 3, below:

TABLE 3

Summary of NNs Training Regressions

| Regression | Temple | Kununurra | Hyderabad | Saskatchewan |
|---|---|---|---|---|
| Yield | >0.97 | >0.98 | >0.98 | >0.96 |
| TSW | >0.99 | >0.99 | >0.99 | >0.99 |

As is evident, the use of neural networks significantly improves learning efficiency, as simulating each episode costs less than two seconds of computation time. If performed solely by the DSSAT module, assuming manually adjusting an irrigation plan takes approximately one hour for each episode, and the rule of thumb that Q-table normally converges after 500 iterations, the time cost would be unmanageable.

States in reinforcement learning may be defined according to crop growth stage and TSW. The state definitions for Temple and Saskatchewan are shown in Table 4 and 5, respectively, and the state definitions for the other two locations are similar.

TABLE 4

State Definition of Case Temple, Texas, United States

| State | ≤540 | (540, 545) | (545, 550) | (550, 560) | >560 |
|---|---|---|---|---|---|
| ≤7 | 1 | 2 | 3 | 4 | 5 |
| ≤15 | 6 | 7 | 8 | 9 | 10 |
| ≤21 | 11 | 12 | 13 | 14 | 15 |
| >21 | 16 | 17 | 18 | 19 | 20 |

TABLE 5

State Definition of Case Saskatchewan, Canada

| State | ≤320 | (320, 325) | (325, 330) | (330, 340) | >340 |
|---|---|---|---|---|---|
| ≤13 | 1 | 2 | 3 | 4 | 5 |
| ≤20 | 6 | 7 | 8 | 9 | 10 |
| ≤27 | 11 | 12 | 13 | 14 | 15 |
| >27 | 16 | 17 | 18 | 19 | 20 |

In Table 4 and Table 5, the header rows include ranges of total soil water with a unit of millimeters. The header columns include time steps. Each entry in the table is a state identifier (state ID). Since the soil and crop type in Temple, Kununurra, and Hyderabad are the same, the division of total soil water levels are the same in those cases. However, as they differ in geolocation, planting date, and weather conditions, the length of the crop seasons and definition of growth stages have some variance. The actions for all four cases are defined in Table 6, below:

TABLE 6

Definition of Actions in All Four Test Cases

| | 1 | 2 | 3 | 4 |
|---|---|---|---|---|
| Temple | wait | 560 | 570 | 580 |
| Kununurra | wait | 560 | 570 | 580 |
| Hyderabad | wait | 560 | 560 | 580 |
| Saskatchewan | wait | 340 | 350 | 360 |

In Table 6, the first action (e.g., Action 1) is to wait, while the rest of the actions include irrigating until a total soil water level reaches a designated target filling point (TPF). The embodiments described herein were compared with fixed scheduling irrigation, which includes applying a fixed amount of water every ten days. Also, the embodiments described herein were compared to threshold-based irrigation, which includes applying a fixed amount of water at a time step if the soil moisture level is below a certain threshold. At the time of the analysis was performed, according to the Food and Agriculture Organization of the United Nations (FAO), international maize and wheat prices are around 200 USD/ton. The cost of irrigation for every 1 ha-mm/ha is about 1 USD. Results shown in Table 7 below were produced based on those price settings. With respect to exploration and exploitation trade-off, to achieve a good balance, $\epsilon$ may be initialized as a value of 0.7 (or similar value) to encourage exploration. As the experience accumulates, the decision making increases its reliance on existing knowledge. As learning continues, $\epsilon$ may decrease. Specifically, if the number of learned episode N<300, $\epsilon \leftarrow 0.7-0.002N$; when N≥300, $\epsilon \leftarrow \sqrt{1/N}$ for each episode.

Figure 12:
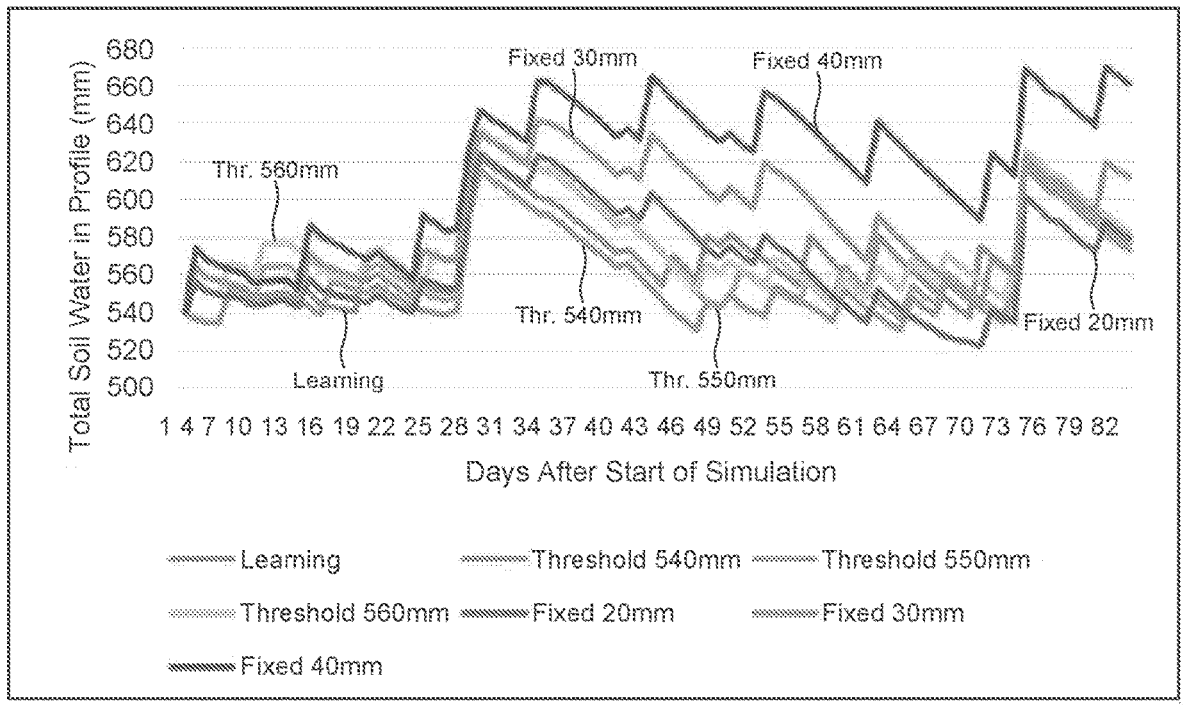
FIG. 12-15 are graphs illustrating comparisons of total soil water profiles under different irrigation methods according to various embodiments of the present disclosure.
Figure 13:
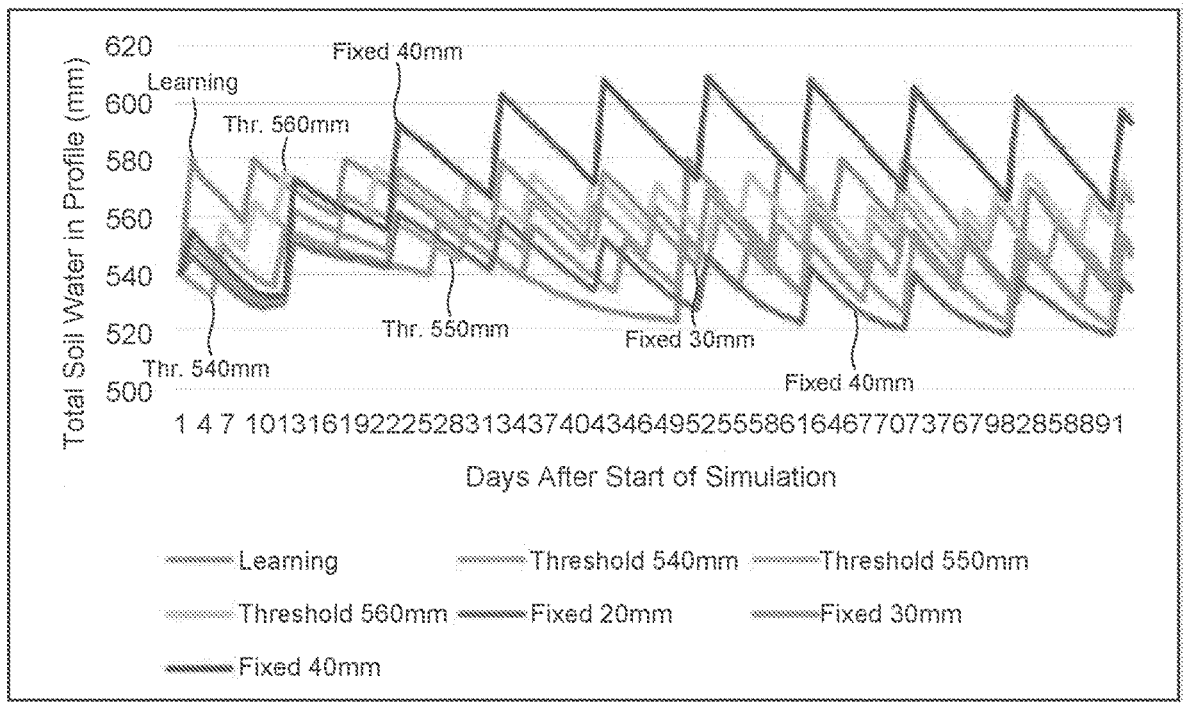
Figure 14:
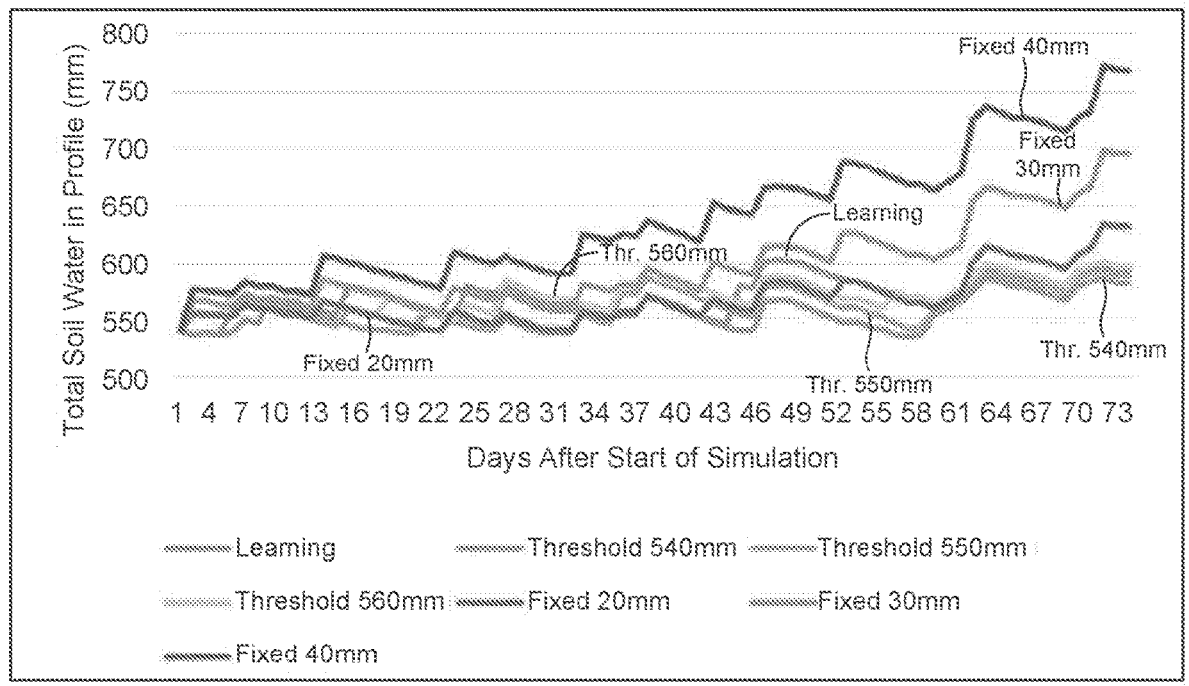
Figure 15:
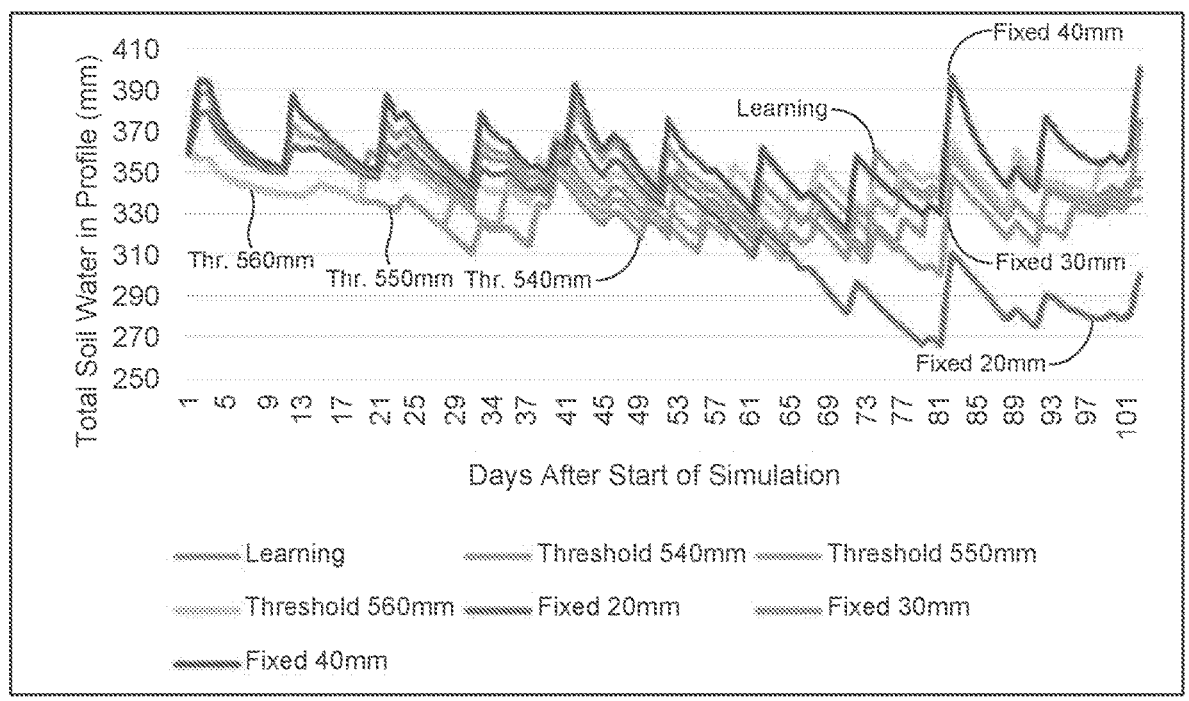

The advantage of utilizing reinforcement learning in water usage can be seen from comparing total soil water curves in FIGS. 10-13. In FIG. 12, the total soil water increases quickly, even if the field does not need that much water. Yet, when water is lost too quickly, in FIG. 13, the fixed method of irrigation does not keep up with crop demand. Although threshold-based method may avoid these problems, they are not flexible enough. For instance, in FIG. 10, embodiments described herein initially keeps the total soil water at a low level; however, it increases the supply of water at later stages. Such arrangement makes perfect sense in agriculture, since at early growth stages, like germination, crops are small and roots are shallow, thus crop water demand is lower compared to later stages. The control application 200, utilizing artificial intelligence, learned this from exploration.

From the result shown in Table 7, Table 8, Table 9, and Table 10, one can see that the performance of the reinforcement learning embodiments described herein stands out in every instance. For example, in Temple, the net return was improved by 27.1% and 15.6%, compared to the average of threshold-based and fixed scheduling method, respectively. In Kununurra, the increased profits are 56.9% and 136.2%; in Hyderabad, 96.4% and 38%, and Saskatchewan, 6.4% and 49.2%. Additionally, the embodiments described herein conserve water and, in most cases, the water consumption under learning method is lower than threshold based and fixed scheduling method. In every tested case, the embodiments described herein outperform the threshold-based method by 46.7%, and fixed scheduling by 59.8% on an average net return.

TABLE 7

Comparison of Performance under Different Irrigation Methods in Temple

|  | Yield (kg/ha) | Total Irrigation (ha-mm/ha) | Net Return (USD/ha) |
| --- | --- | --- | --- |
| Learning | 9224 | 236 | 1608 |
| Threshold 540 mm | 6576 | 160 | 1155 |
| Threshold 550 mm | 7530 | 200 | 1306 |
| Threshold 560 mm | 7876 | 240 | 1335 |
| Fixed 20 mm | 6993 | 180 | 1218 |
| Fixed 30 mm | 8948 | 270 | 1519 |
| Fixed 40 mm | 8975 | 360 | 1435 |

TABLE 8

Comparison of Performance under Different Irrigation Methods in Kununurra

|  | Yield (kg/ha) | Total Irrigation (ha-mm/ha) | Net Return (USD/ha) |
| --- | --- | --- | --- |
| Learning | 11279 | 303 | 1952 |
| Threshold 540 mm | 6530 | 280 | 1026 |
| Threshold 550 mm | 8732 | 280 | 1406 |
| Threshold 560 mm | 8393 | 380 | 1298 |
| Fixed 20 mm | 3482 | 200 | 496 |
| Fixed 30 mm | 4671 | 300 | 634 |
| Fixed 40 mm | 8743 | 400 | 1348 |

TABLE 9

Comparison of Performance under Different Irrigation Methods in Hyderabad

|  | Yield (kg/ha) | Total Irrigation (ha-mm/ha) | Net Return (USD/ha) |
| --- | --- | --- | --- |
| Learning | 5493 | 125 | 973 |
| Threshold 540 mm | 2100 | 80 | 340 |
| Threshold 550 mm | 3217 | 120 | 523 |
| Threshold 560 mm | 3815 | 140 | 623 |
| Fixed 20 mm | 4079 | 160 | 655 |
| Fixed 30 mm | 5303 | 240 | 820 |
| Fixed 40 mm | 4790 | 320 | 638 |

TABLE 10

Comparison of Performance under Different Irrigation Methods in Saskatchewan

|  | Yield (kg/ha) | Total Irrigation (ha-mm/ha) | Net Return (USD/ha) |
| --- | --- | --- | --- |
| Learning | 8146 | 210 | 1419 |
| Threshold 540 mm | 7377 | 220 | 1255 |
| Threshold 550 mm | 7893 | 200 | 1378 |
| Threshold 560 mm | 8031 | 240 | 1366 |
| Fixed 20 mm | 6478 | 220 | 1075 |
| Fixed 30 mm | 6680 | 330 | 1006 |
| Fixed 40 mm | 6057 | 440 | 771 |

Agricultural irrigation plays a critical role in addressing the challenge of fresh water shortage. The progress of wireless sensor and internet technologies allows advanced site-specific variable rate irrigation, which has not been fully exploited yet. A reinforcement learning based control approach is proposed. Its training can be carried out either through online crop growth season or offline simulations. A neural network infrastructure is built to facilitate efficient trainings. Its successful implementation opens a promising alternative in future computational agricultural research. Simulations for different crop types at various geographic locations show that the proposed method outperforms fixed irrigation scheduling by 59.8% and threshold based approach by 46.7% on average net return.

Figure 16:
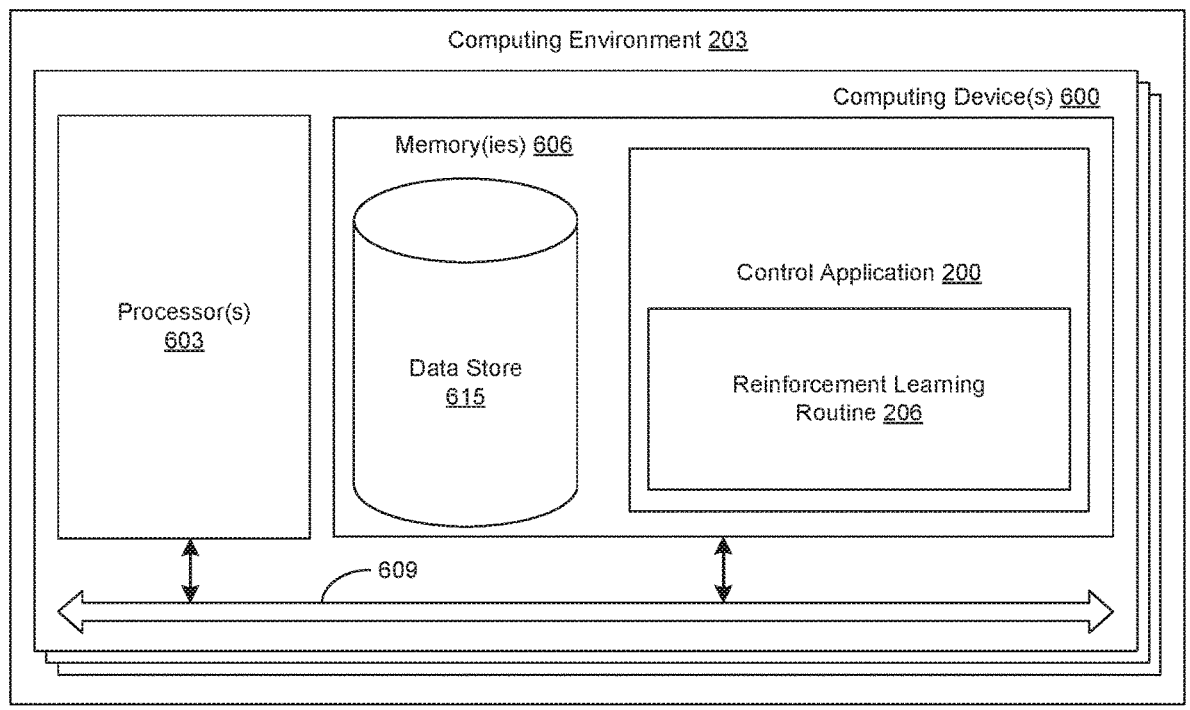
FIG. 16 is a schematic block diagram that provides one example illustration of a computing environment that may be employed in a networked environment according to various embodiments of the present disclosure.

With reference to FIG. 16, shown is a schematic block diagram of the computing environment 203 according to an embodiment of the present disclosure. The computing environment 203 includes one or more computing devices 600. Each computing device 600 includes at least one processor circuit, for example, having a processor 603 and a memory 606, both of which are coupled to a local interface 609. To this end, each computing device 600 may comprise, for example, a microcontroller, at least one server computer, or like device. The local interface 609 may comprise, for example, a data bus with an accompanying address/control bus or other bus structure as can be appreciated.

Stored in the memory 606 are both data and several components that are executable by the processor 603. In particular, stored in the memory 606 and executable by the processor 603 is the control application 200, and potentially other applications. Also stored in the memory 606 may be a data store 615 and other data. In addition, an operating system may be stored in the memory 606 and executable by the processor 603.

The operations of the control application 200 and other various systems described herein may be embodied in software or code executed by general purpose hardware as discussed above, as an alternative the same may also be embodied in dedicated hardware or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits (ASICs) having appropriate logic gates, field-programmable gate arrays (FPGAs), or other components, etc. Such technologies are generally well known by those skilled in the art and, consequently, are not described in detail herein.

Also, the operations of the control application 200 can be implemented by logic or an application that comprises software or program code can be embodied in any non-transitory computer-readable medium for use by or in connection with an instruction execution system such as, for example, a processor in a computer system or other system. In this sense, the logic may comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system.

Further, any logic or application described herein, including the operations performed by the control application 200, may be implemented and structured in a variety of ways. For example, one or more applications described may be implemented as modules or components of a single application. Further, one or more applications described herein may be executed in shared or separate computing devices or a combination thereof. For example, a plurality of the applications described herein may execute in the same computing device, or in multiple computing devices in a same computing environment. Additionally, it is understood that terms such as "application," "service," "system," "engine," "module," and so on may be interchangeable and are not intended to be limiting.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims and clauses.

Clause 1. A system for reinforcement learning-based irrigation control to maintain or increase a crop yield or reduce water use, comprising: at least one computing device; and program instructions stored in memory and executable by the at least one computing device that, when executed, direct the at least one computing device to: determine an optimal irrigation schedule for at least one crop in at least one region of a field by executing a reinforcement learning (RL) routine, where, for a given state of a total soil moisture, the reinforcement learning (RL) routine is configured to: perform an action, the action comprising waiting or irrigating the at least one crop; and assign an immediate reward to a state-action pair, the state-action pair comprising the given state of the total soil moisture and the action performed; and instruct an irrigation system to apply irrigation to at least one crop in accordance with the optimal irrigation schedule determined, wherein the optimal irrigation schedule comprises an amount of water and a determined time at which the amount of water should be applied.

Clause 2. The system of clause 1, wherein the optimal irrigation schedule is determined using at least one of: a real-time soil moisture value, a near real-time soil moisture value, a recent or near real-time evapotranspiration metric, a predictive evapotranspiration (ET) metric, or a weather forecast metric.

Clause 3. The system of any of clauses 1-2, further comprising a cascading neural network configured to generate a crop yield.

Clause 4. The system of any of clauses 1-3, wherein the cascading neural network configured to generate the crop yield comprises: a first neural network configured to receive, as an input, at least one of irrigation data and weather data, wherein the first neural network is configured to provide a total soil water (TSW) value determined based at least in part on the input; and a second neural network configured to receive the total soil water as an input, wherein the second neural network is configured to generate the crop yield based at least in part on the total soil water.

Clause 5. The system of any of clauses 1-4, wherein the system further comprises a decision support system for agrotechnology transfer (DSSAT) module configured to communicate with the cascading neural network over a network.

Clause 6. The system of any of clauses 1-5, wherein: the first neural network is configured to receive training data from the DSSAT module and train using the training data prior to generating the total soil water (TSW) value; and the second neural network is configured to receive training data from the DSSAT module and train using the training data before generating the crop yield.

Clause 7. The system of any of clauses 1-6, wherein the at least one computing device is a microcontroller implemented in a mobile irrigation machine; and the irrigation system is instructed to apply irrigation to at least one crop in accordance with the optimal irrigation schedule by converting the optimal irrigation schedule to a suitable signal for interpretation by the irrigation system.

Clause 8. The system of any of clauses 1-7, further comprising at least one soil moisture sensor positioned in the at least one region of the field; and wherein the optimal irrigation schedule is determined based at least in part on a soil moisture measurement obtained by the at least one soil moisture sensor.

Clause 9. A computer-implemented method for reinforcement learning-based irrigation control to maintain or increase a crop yield or reduce water use, comprising: determining, by at least one computing device, an optimal irrigation schedule for at least one crop in at least one region of a field by executing a reinforcement learning (RL) routine, where, for a given state of a total soil moisture, the reinforcement learning (RL) routine comprises: simulating, by the at least one computing device, an action, the action comprising waiting or irrigating the at least one crop; and assigning, by the at least one computing device, an immediate reward to a state-action pair, the state-action pair comprising the given state of the total soil moisture and the action performed; and instructing an irrigation system to apply irrigation to at least one crop in accordance with the optimal irrigation schedule determined, wherein the optimal irrigation schedule comprises an amount of water and a determine time at which the amount of water should be applied.

Clause 10. The computer-implemented method of clause 9, wherein the optimal irrigation schedule is determined using at least one of: a real-time soil moisture value, a near real-time soil moisture value, a predictive evapotranspiration (ET) metric, or a weather forecast metric.

Clause 11. The computer-implemented method of any of clauses 9-10 further comprising generating, by a cascading neural network, a crop yield, wherein the crop yield is used to assign the immediate reward to the state-action pair.

Clause 12. The computer-implemented method of any of clauses 9-11, wherein generating, by the cascading neural network, the crop yield further comprises: receiving, by a first neural network, as an input, at least one of irrigation data and weather data; providing, by the first neural network, a total soil water (TSW) value determined based at least in part on the input; receiving, by a second neural network, the total soil water as an input; and generating, by the second neural network, the crop yield based at least in part on the total soil water.

Clause 13. The computer-implemented method of any of clauses 9-12, further comprising: receiving, by the first neural network, training data from a decision support system for agrotechnology transfer (DSSAT) module; training, by the first neural network, using the training data prior to generating the total soil water (TSW) value; receiving, by the second neural network, training data from the DSSAT module; and training, by the second neural network, using the training data prior to generating the crop yield.

Clause 14. The computer-implemented method of any of clauses 9-13, wherein the at least one computing device is a microcontroller implemented in a mobile irrigation machine; and further comprising applying, by the microcontroller, irrigation to at least one crop in accordance with the optimal irrigation schedule by converting the optimal irrigation schedule to a suitable signal for interpretation by the irrigation system.

Clause 15. The computer-implemented method of any of clauses 9-14, wherein the optimal irrigation schedule is determined based at least in part on a soil moisture measurement obtained by at least one soil moisture sensor positioned in the at least one region of the field.

Therefore, the following is claimed:

1. A system for reinforcement learning-based irrigation control to maintain or increase a crop yield or reduce water use, comprising:
at least one computing device; and
program instructions stored in memory and executable by the at least one computing device that, when executed, direct the at least one computing device to:
determine an optimal irrigation schedule for at least one crop in at least one region of a field by executing a reinforcement learning (RL) routine, where, for a given state of a total soil moisture, the reinforcement learning (RL) routine is configured to:
perform an action, the action comprising waiting or irrigating the at least one crop;
execute a cascading neural network comprising a first neural network and a second neural network and generate the crop yield for the at least one crop based on the performed action by:
executing a first neural network that receives, as an input, at least one of irrigation data or weather data and determines a total soil water (TSW) value determined based at least in part on the input, wherein the first neural network receives training data from a crop growth computer model and is trained using the training data prior to generating the total soil water (TSW) value; and
executing a second neural network that receives the total soil water as an input and generates the crop yield based at least in part on the total soil water, wherein the second neural network receives training data from the crop growth computer model and is trained using the training data before generating the crop yield;
assign a reward to a state-action pair, the state-action pair comprising the given state of the total soil moisture and the action performed, wherein the reward is assigned based on a predicted crop yield generated by the cascading neural network; and
instruct an irrigation system to apply irrigation to at least one crop in accordance with the optimal irrigation schedule determined, wherein the optimal irrigation schedule comprises an amount of water and a determined time at which the amount of water should be applied.

2. The system of claim 1, wherein the optimal irrigation schedule is determined using at least one of: a real-time soil moisture value, a near real-time soil moisture value, a predictive evapotranspiration (ET) metric, or a weather forecast metric.

3. The system of claim 1, wherein the system further comprises a decision support system for agrotechnology transfer (DSSAT) computing device.

4. The system of claim 1, wherein:
the at least one computing device is a microcontroller implemented in a mobile irrigation machine; and
the irrigation system is instructed to apply irrigation to at least one crop in accordance with the optimal irrigation schedule by converting the optimal irrigation schedule to a suitable signal for interpretation by the irrigation system.

5. The system of claim 1, further comprising at least one soil moisture sensor positioned in the at least one region of the field; and
wherein the optimal irrigation schedule is determined based at least in part on a soil moisture measurement obtained by the at least one soil moisture sensor.

6. A computer-implemented method for reinforcement learning-based irrigation control to maintain or increase a crop yield or reduce water use, comprising:

determining, by at least one computing device, an optimal irrigation schedule for at least one crop in at least one region of a field by executing a reinforcement learning (RL) routine, where, for a given state of a total soil moisture, the reinforcement learning (RL) routine comprises:

simulating, by the at least one computing device, an action, the action comprising waiting or irrigating the at least one crop;

generating, by a cascading neural network comprising a first neural network and a second neural network, a crop yield for the at least one crop based on the simulated action by:

receiving, by the first neural network, as an input, at least one of irrigation data or weather data;

providing, by the first neural network, a total soil water (TSW) value determined based at least in part on the input, wherein the first neural network receives training data from a crop growth computer model and is trained using the training data prior to generating the total soil water (TSW) value;

receiving, by the second neural network, the total soil water as an input; and generating, by the second neural network, the crop yield based at least in part on the total soil water, wherein the second neural network receives training data from the crop growth computer model and is trained using the training data before generating the crop yield; and assigning, by the at least one computing device, a reward to a state-action pair, the state-action pair comprising the given state of the total soil moisture and the simulated action, wherein the reward is assigned based on a predicted crop yield generated by the cascading neural network; and instructing an irrigation system to apply irrigation to at least one crop in accordance with the optimal irrigation schedule determined, wherein the optimal irrigation schedule comprises an amount of water and a determined time at which the amount of water should be applied.

7. The computer-implemented method of claim 6, wherein the optimal irrigation schedule is determined using at least one of: a real-time soil moisture value, a near real-time soil moisture value, a predictive evapotranspiration (ET) metric, or a weather forecast metric.

8. The computer-implemented method of claim 6, wherein the at least one computing device is a microcontroller implemented in a mobile irrigation machine; and further comprising applying, by the microcontroller, irrigation to at least one crop in accordance with the optimal irrigation schedule by converting the optimal irrigation schedule to a suitable signal for interpretation by the irrigation system.

9. The computer-implemented method of claim 6, wherein the optimal irrigation schedule is determined based at least in part on a soil moisture measurement obtained by at least one soil moisture sensor positioned in the at least one region of the field.

10. The system of claim 1, wherein the reward assigned to the state-action pair is one of an immediate reward or a delayed reward to the state-action pair.

11. The system of claim 10, wherein:

the reward assigned to the state-action pair comprises the delayed reward; and the at least one computing device is further directed to execute a temporal difference learning algorithm to account for the delayed reward.

12. The computer-implemented method of claim 6, wherein assigning, by the at least one computing device, the reward to the state-action pair further comprises assigning one of an immediate reward or a delayed reward to the state-action pair.

13. The computer-implemented method of claim 12, wherein:

the reward assigned to the state-action pair comprises the delayed reward; and the computer-implemented method further comprises executing a temporal difference learning algorithm to account for the delayed reward.

14. The computer-implemented method of claim 6, wherein the at least one crop is at least one of wheat or maize.

15. A non-transitory computer readable storage medium storing software thereon, the software comprising instructions configured to cause at least one processor of at least one computer to perform steps comprising:

determining an optimal irrigation schedule for at least one crop in at least one region of a field by executing a reinforcement learning (RL) routine, where, for a given state of a total soil moisture, the reinforcement learning (RL) routine comprises:

simulating an action, the action comprising waiting or irrigating the at least one crop;

generating, by a cascading neural network comprising a first neural network and a second neural network, a crop yield for the at least one crop based on the simulated action by:

receiving, by the first neural network, as an input, at least one of irrigation data or weather data;

providing, by the first neural network, a total soil water (TSW) value determined based at least in part on the input, wherein the first neural network receives training data from a crop growth computer model and is trained using the training data prior to generating the total soil water (TSW) value;

receiving, by the second neural network, the total soil water as an input; and generating, by the second neural network, the crop yield based at least in part on the total soil water, wherein the second neural network receives training data from the crop growth computer model and is trained using the training data before generating the crop yield; and assigning a reward to a state-action pair, the state-action pair comprising the given state of the total soil moisture and the simulated action, wherein the reward is assigned based on a predicted crop yield generated by the cascading neural network; and instructing an irrigation system to apply irrigation to at least one crop in accordance with the optimal irrigation schedule determined, wherein the optimal irrigation schedule comprises an amount of water and a determined time at which the amount of water should be applied.

16. The non-transitory computer readable storage medium of claim 15, wherein the optimal irrigation schedule is determined using at least one of: a real-time soil moisture value, a near real-time soil moisture value, a predictive evapotranspiration (ET) metric, or a weather forecast metric.

17. The non-transitory computer readable storage medium of claim 15, wherein the optimal irrigation schedule is determined based at least in part on a soil moisture measurement obtained by at least one soil moisture sensor positioned in the at least one region of the field.

18. The non-transitory computer readable storage medium of claim 15, wherein assigning the reward to the state-action pair further comprises assigning one of an immediate reward or a delayed reward to the state-action pair.

19. The non-transitory computer readable storage medium of claim 18, wherein:
- the reward assigned to the state-action pair comprises the delayed reward; and
- the steps further comprise executing a temporal difference learning algorithm to account for the delayed reward.

20. The non-transitory computer readable storage medium of claim 18, wherein the steps further comprise applying irrigation to at least one crop in accordance with the optimal irrigation schedule by converting the optimal irrigation schedule to a suitable signal for interpretation by an irrigation system.

* * * * *